US006326528B1

(12) United States Patent
Simmonds et al.

(10) Patent No.: US 6,326,528 B1
(45) Date of Patent: *Dec. 4, 2001

(54) WHEAT ALEURONE REGULATORY REGION

(75) Inventors: John Simmonds, Nepean; Leslie Cass, Carp; Linda Harris, Greely; Sharon Allard, Nepean, all of (CA)

(73) Assignee: Her Majesty the Queen in right of Canada, as represented by the Minister of Agriculture, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,777

(22) Filed: Oct. 14, 1999

Related U.S. Application Data

(63) Continuation-in-part of application No. 09/102,046, filed on Jun. 22, 1998, now Pat. No. 6,013,862.

(30) Foreign Application Priority Data

May 7, 1998 (CA) .................................................. 2230975

(51) Int. Cl.[7] .............................. A01H 1/00; A01H 5/00; C12N 15/82; C12N 15/87

(52) U.S. Cl. ...................... 800/287; 800/298; 435/468; 435/419; 536/23.1

(58) Field of Search .................................... 800/287, 295, 800/320.3, 298; 435/419, 468; 536/23.1

(56) References Cited

U.S. PATENT DOCUMENTS 5,525,716  6/1996  Olsen et al. .
6,013,862 * 1/2000  Simmonds et al. .

FOREIGN PATENT DOCUMENTS 2110772     6/1995  (CA) .
WO 95/23230  8/1995  (WO) .

OTHER PUBLICATIONS

Leah et al. Identification of an enhancer/silencer sequence directing the aleurone–specific expression of a barley chitinase gene. Plant J. 6(4) 1994, pp. 579–589.*

Skriver et al, Structure and expression of the barley lipid transfer protein gene Ltp1, Plant Molecular Biology 18: 585–589, 1992.

Dieryck et al, Nucleotide sequence of a cDNA encoding a lipid transfer protein from wheat (*Triticum durum* Desf.), Plant Molecular Biology, 19:707–709, 1992.

Linnestad et al, Promoter of a Lipid Transfer Protein Gene Expressed in Barley Aleurone Cells Contains Similar myb and myc Recognition Sites as the Maise Bz–McC Allele, Plant Physiol. (1991) 97, 841–843.

Jakobsen et al, Barley aleurone cell development: molecular cloning of aleurone–specific cDNAs from immature grains, Plant Molecular Biology 12:285–93, 1989.

Kalla et al 1994, The promoter of the barley aleurone–specific gene encoding a putative 7kDa lipid transfer protein confers aleurone cell–specific expression in transgenic rice, Plant Journal (1994) 6(6):849–860.

Molina et al, Developmental and pathogen–induced expression of three barley genes encoding lipid transfer proteins, The Plant Journal (1993) 4(6):983–991).

Odell, J.T. et al, Identification of DNA sequences required for activity of the cauliflower mosaic virus 35S promoter, Nature vol. 313–810–812, 1985.

McElroy D., et al Isolation of An Efficient Actin Promoter for use in Rice Transformation, The Plant Cell vol. 2:163–171 (1990).

* cited by examiner

*Primary Examiner*—Andrew Wang
*Assistant Examiner*—Konstantina Katcheves
(74) *Attorney, Agent, or Firm*—Morgan, Lewis & Bockius LLP

(57) ABSTRACT

This invention is directed to a regulatory region obtained from a wheat aleurone gene LtpW1. This regulatory region, or truncated derivatives of this regulatory region, can be used to express heterologous genes of interest within aleurone cells of a plant. Furthermore, this invention is directed to a truncated LtpW1 regulatory region that exhibits constructive activity within both monocot and dicot plants. This invention is also directed to vectors comprising these regulatory regions operatively linked with a heterologous gene of interest, as well as plant cell cultures and transgenic plants comprising these vectors. A method for the preparation of a plant using the regulatory regions of this invention are also disclosed.

20 Claims, 14 Drawing Sheets

FIG. 3

*SEQ ID NO:1 (687 bp) >

-688 TCTAGAGAAAGAGTTTTAGACCGGAGGTATTTGTTAGGAAGTACTTCTTGCCATACTAGT

-628 TTCAATAAAGTAGCTTGAAAAGACATTTGTTAAGCAACCATGTGTTTTTAATATGAAGAT

-568 CCTCAATACCGAGAGCCTTTGGTCCCATGGATGACACAAAACTTCCCACTTGTTTTTTTT

*SEQ ID NO:2 (473 bp) >

-508 TTTTGTGTGTGTGTGGGTAAACTTCCCACTTGGTTAACCTATACTTCCGCTTATGTTCAT

-448 CACTTTGCCAGAAAATTGCATATGTGAAGGAAGTGCCAATATTTAATACCGTCTGGTGTT

-388 ATAAATTCATCTCCCAAAATTATTGGAGTTGAAGATTCACTTGAAAAAATAATTTGACAT

-328 ATTAAAGATGTTGCCCTTGCGCGGGGTATCTGCAAATTGAGGATCCAAGGGACGATTGCA

-268 TCCAGTTCTAAACACACCATTATGATTTCAGTGATAATGCATGCTT*CCAAA*GCCCAGCTG

*SEQ ID NO:3 (206 bp) >

-208 CAAGCTTGGGCCATCCTTCGGAAGGGAAAAAGAAAAAGGGGTCCTGCTGCACCAGCGACT

-148 AAACCATCCACGCATCTCTCGCTCGAACCCC*TATTTAA*GCCCCTCCATTCTTCCCTACAT

-88 TCTCC*ACACAA*CCACGAGTTGCTCATCTCTCCACCCAATCATCACTAGCTAATACGGTGC

*+1
                                =
-28 ACTGTTAGCTACAGACCAAGAAGTGATC<u>ATGGCCCGCGCTCAGGTAATGCTCATGGCCGT</u>

33 <u>CGCCTTGGTGCTCATGCTCGCGGCGGTCCCGCGCGCTGCCGTGGCCATCGACTGCGGCCA</u>

93 <u>CGTTGACAGCTTGGTGAGACCCTGCCTGAGCTACGTTCAGGGCGGCCCCGGCCCGTCTGG</u>

153 <u>GCAGTGCTGCGACGGCGTCAAGAACCTCCATAACCAGGCGCGATCCCAGAGCGATCGCCA</u>

213 <u>AAGCGCTTGCAACTGCCTCAAGGGGATCGCTCGTGGCATCCACAATCTCAACGAGGACAA</u>

273 <u>CGCCCGCAGCATCCCCCCCAAGTGCGGTGTCAACCTCCCATACACCATCAGTCTCAACAT</u>

333 <u>CGACTGCAGCAG</u>GTGATTAATTCACATGCAAGCATATATATATGAACACTCATCCACGTA

393 AAATTTATTGATATTAACATTAATCAAATCTTTGCACTGCAG<u>GGTGTAATGG</u>GCGACGAT

453 CCGTCAAGCTGGTGCTCAGCTCATCCATCCACGTGGAGTTGAAGCGCGCAGCCTCTATCC

513 CTATGTAGTATGGTCACTAGTTATGCGAGTTTATACTGAATATGAATAAGAACTCTCTCC

573 AGCTGGCTTGCTGGTACTCCTCTGGAGGAGATCAGTATCTGTGTACCTGAGAGTTGAGAG

633 TTTGTACCATGGGCACTCCCAGTGTTTATGGACTTTAATACATACAACTCGTTCTGTTCA

693 GCGTGTGACTTATCTTTGTTTCCTCACGTTCGCCTGTCATATACTCCTTCCATCCGGTAT

753 TAGTTGGCGTTCAAACGGATATATCTAGA

FIG. 4(a)-1

```
-679 GTTTTAGACCGGAGGTATTTGTTAGGAAGTACTTCTTGCCATACTAGTTTCAATAAAGTA
     |||| ||| ||  |   | |      |           |     | |   |      |||
-700 GTTTGATAACAAAGTAGTAAAAAAACTAAAGTATTAAAAACTGCAGTAATTTTACGTGTA

-619 GCTTGAAAAGACATTTGTTAAGCAACCATGTGTTTTTAATATGAAGATCCTCAATACCGA
     | | |||||| ||  |||      |   |  ||    ||     | |   |    ||  ||
-630 GATAGAAAATACCATGGTTTTAATATAATAATATTTTTGCAGTATTCACAATGTAGAGA

-559 GAGCCTTTGGTCCCATGGATGACACAAAACT..............................
       |  |||| | |       |
-570 AACTGTTTGATTACGCCACATATTACTGCAGTTTAGATCGAGCAAGTACACGGGAAGAAG

-528 .........TCCCACTTGTTTTTTTTTTTGTGTGTGTGTGGGTAAACTTCCCACTTGGT
              ||||||  || ||||  |       | |  H||    | ||
-510 ATAACGACGTCCCACCCCTTCTTTTCGCCTTCTCTGTTTTTAAAAAGAGGTCTGGGGTT

-477 TAACCTATACTTCCGCTTATGTTCATCACTTTGCCAGAAAATTGCATATGTGAAGGAAGT
     ||   ||   |||  |  |  | |          ||  |  |    | |   |    ||
-450 AGTTTTTCAATACTGCAGTTTTAAAATCACAATTCTTAGAGGCAACCAAACACCTCATT

-417 GCCAATATTTAATACCGTCTGGTGTTATAAATTCATCTCCCAAAATTATTGGAGTTGAAG
     | ||||             |      |        || |||||| |
-390 GTAAATAAAACTATGATAATCTCCAAAACTGCAGTATTCTAAAAATACTAC..........

-357 ATTCACTTGAAAAAATAATTTGACATATTAAAGATGTTGCCCTTGCGCGGGGTATCTGCA
     ||||||  |||| ||  |  |  |   |                              | ||
-339 ..........AAAAATTCTTTGTTATCAAACAGGGCCTAAGGAGTTAAAAAAATTTAGCC

-297 AATTGAGGATCCAAGGGACGATTGCATC.....CAGTTCTAAACACACCATTATGATTTC
      |   |  |  |||              |||| | |||||      ||||
-289 GTAACTGAGACTCGGCGAGGCACCAGCAGCTAGCAGTCATCAACACT......TGATGGT
                                      *SEQ ID NO:3 >
-242 AGTGATAATGCATGCTTCCAAAGCCCAGCTGCAAGCTTGGGCCATCCTTCGGAAGGGAAA
     | | |   | ||    | |  |    |     |    |||   |           |  |
-235 TGGCAAAGGCGAGTCGACGTGTCGCGGGGCTCGGCCTGAGCGGGAGATACAATCTGTTCT

-182 AAGAAAAAGGGGTCCTGCTGCACCAGCGACTAAACCATCCACGCATCTCTCGCTCGAACC
      ||   ||| || ||  ||||||||||| |||||||| ||||||||||||||||||||||
-175 CCAGTAACCCCGTCGATTTGGCCCGCCGACTAAAGCATCCAGGCATCTCTCGCTCGAACC

-122 CCTATTTAAGCCCCTCCATTCTTCCCTACATTCTCCACACAACCACGAGTTGCTCATCTC
     ||||||||||||||||||||||| |||| |||||||||||| | ||||||||||
-115 CCTATTTAAGCCCCTCCATTCCTCCCAACATTCTCCACACCTCCACGAGTTGC.......
                                                              *
-62  TCCACCCAATCATCACTAGCTAATACGGTGCACTGTTAGCTACAGACCAAGAAGTGATCA
             ||||||||||| ||||| || |||||||||||||||||||| |||||||||||
-53  ........TCATCACTAGCTAGTACGTTGTACTGTTAGCTACAGATTAAGAAGTGATCA
```

FIG. 4(a)-2

```
  2 TGGCCCGCGCTCAGGTAATGCTCATGGCCGTCGCCTTGGTGCTCATGCTCGCGGCGGTCC
    ||||||||||||||||| ||||||||||| |||||||||||| |||||| |||||| ||
  2 TGGCCCGCGCTCAGGTACTGCTCATGGCCGCCGCCTTGGTGCTGATGCTCACGGCGGCCC

62 CGCGCGCTGCCGTGGCCATCGACTGCGGCCACGTTGACAGCTTGGTGAGACCCTGCCTGA
    ||||||||||||||| || ||||||||| |||||||||| | ||| ||| |||||||
 62 CGCGCGCTGCCGTGGCCCTCAACTGCGGCCAGGTTGACAGCAAGATGAAACCTTGCCTGA

122 GCTACGTTCAGGGCGGCCCCGGCCCGTCTGGGCAGTGCTGCGACGGCGTCAAGAACCTCC
    ||||||||||||||||||||||||||| || | |||||| |||||||| | | ||||
122 CCTACGTTCAGGGCGGCCCCGGCCCGTCCGGCGAATGCTGCAACGGCGTCAGGGATCTCC

182 ATAACCAGGCGCGATCCCAGAGCGATCGCCAAAGCGCTTGCAACTGCCTCAAGGGGATCG
    |||||||||||| |||| | ||||| ||||||| || ||||||||||||| ||||||||||
182 ATAACCAGGCGCAATCCTCGGGCGACCGCCAAACCGTTTGCAACTGCCTGAAGGGGATCG

242 CTCGTGGCATCCACAATCTCAACGAGGACAACGCCCGCAGCATCCCCCCCAAGTGCGGTG
    |||| |||||||||||||||||| |||||||| ||||||||||| |||||||| ||
242 CTCGCGGCATCCACAATCTCAACCTCAACAACGCCGCCAGCATCCCCTCCAAGTGCAATG

302 TCAACCTCCCATACACCATCAGTCTCAACATCGACTGCAGCAGGTGATTAATTCACATGC
    ||||| ||||||||||||||| | |||||||||| ||||||||| |
302 TCAACGTCCCATACACCATCAGCCCCGACATCGACTGCTCCAGGTGATTAAATTTACACT

362 AAGCATA.............................TATATATGAAC
     | |                                |||||| ||||
363 CATCCAGAGTGAAATCTTTAAAAAGAACTATATTTACGAACGGAGTGAGTATATAGGAAC

380 ACTCATCCACGTAAAATTTATTGATATTAACATTAATCAAATCTTTGCA.CTGCAGGGTG
    | |||||||||||||||| |||||||||||||||||||| | | |||||||| |
423 ATTCATCCACGTAAAATTTGTTGATATTAACATTAACACGCATGATTGACCTGCAGGATT

440 TAATGGGCGACGATCCGTCAAGCTGGTGCTCAGCTCATCCATCCACGTGGAGTTGAAGCG
    || || ||||||||||||||||||||||||||||||||||| |||||||||| |||||||
483 TACTGAGCGACGATCCGTCAAGCTGGTGCTCAGCTCATCGATCCACGTGGAGCTGAAGCG

500 CGCAGCCTCTATCCCTATGTAGTATGGTCACTAGTTATG.CGAGTTTATACTGAATATGA
    ||||||||| ||||||||||||||||| || ||||||| ||||||||| ||||
543 CGCAGCCTCTGTCCCTATGTAGTATGGCTACCAGTTATGCCGAGTTTATGCTGA......

559 ATAAGAACTCTCTCCAGCTGGCTTGCTGGTACTCCTCTGGAGGAGATCAGTATCTGTGTA
    ||||||||||||||            |||||||| ||||||||||||||||||||| |||
597 ATAAGAACTCTCTCCT...........GTACTCCTTGGAGGAGATCAGTATCTATGTA

619 CCTGAGAGTTGAGAGTTTGTACCATGGGCACTCCCAGTGTTTATGGACTT
    | |||||||||||||||||||||||||| |||||||||||||||||||||
645 CGTGAGAGTTGAGAGTTTGTACCATGGCACTCCCAGTGTTTATGGACTA
```

FIG. 4(b)-1

```
-681 AAAGAGTTTTAGACCGGAGGTATTTGTTAGGAAGTACTTCTTGCCATACTAGT..TTCAA
      ||      |   ||  ||   ||  ||      ||      |||  |||||
-822 AACCGTGGCCTAAAAATAAGCCGATGAGGATAAATAAAATGTGGTGGTACAGTACTTCAA

-623 TAAAGTAGCTTGAAAAGACATTTGTTAAGCAACCATGTGTTTTTAATATGAAGATCCTCA
      |   |  ||  ||||  | ||   ||  | |  | |                || |
-762 GAGGTTTACTCATCAAGAGGATGCTTTTCCGATGAGCTCTAGTAGTACATCGGACCTCAC

-563 ATACCGAGAGCCTTTGGTCCCATGGATGACACAAAACTTCCCACTTGTTTTTTTTTTTTG
     |||||    |   |   ||     | ||      |    |    ||||  ||| ||
-702 ATACCTCCATTGTGGTGAAATATTTTGTGCTCATTTAGTGATGGGTAAATTTTGTTTATG

-503 TGTGTGT..GTGGGTAAACTTCCCACTTGGTTAACCTATACTTCCGCTTATGTTCATCAC
      |  | ||   |  | |||   |||    | ||  || |  |  | ||   |     ||
-642 TCACTCTAGGTTTTGACATTTCAGTTTTGCCACTCTTAGGTTTTGACAAATAATTTCCAT

-445 TTTGCC.....AGAAAATTGCATATGTGAAGGAAGTGCCAATATTTAATACCGTCTGGTG
      |  ||      ||  || |||      |   |   ||| |  | |  ||       ||
-582 TCCGCGGCAAAAGCAAAACAATTTTATTTTACTTTTACCACTCTTAGCTTTCACAATGTA

-390 TTATAAATTCATCTCCCAAAATTATTGGAGTTGAAGATTCACTTGAAAAAATAATTTGAC
      |  ||||| |   |||   |||||  ||   ||      |  |||||||||| |  ||
-522 TCACAAATGCCACTCTAGAAATTC.TGTTTATGCCACAGAATGTGAAAAAAAACACTCAC

-330 ATATTA......AAGATGTTGCCCTTGCGCGGGGTATCTGCAAATTGAGGATCCAAGGGA
     ||||        |||  ||||                |||||| ||    |
-463 TTATTTGAAGCCAAGGTGTTCATGGCATGGAAATGTGACATAAAGTAACGTTCGTGTATA

-276 CGATTGCATCCAGT...TCTAAACACACCATTATGATTTCAGTGATAATGCATGCTTCCA
      ||   ||          ||  |||| |     |   |||       |    |   ||  |
-403 AGAAAAAATTGTACTCCTCGTAACAAGAGACGGAAACATCATGAGACAATCGCGTTTGGA
                      *SEQ ID NO:3 >
-219 AAGCCCAGCTGCAAGCTTGGGCCATCCTTCGGAAGGGAAAAAGAAAAAGGGGTCCTGCTG
      |  ||   ||  ||   ||||    ||  |     ||| ||         ||  |||   ||
-343 AGGCTTTGCATCACCTTTGGATGATGCGCATGAATGG..........AGTCGTCTGCTTG

-159 CACCAGCGACTAAACCATCCACGCATCTCTCGCTCGAACCCCTATTTAAGCCCCTCCATT
      |      |||  ||||  |   |    | ||  ||| |||  |     |    |    ||
-293 CTAGCCTTCGCCTACCGCCCACTGAGTCCGGGCGGCAACTACCATCGGCGAACGACCCAG

-99  CTTCCCTACATTCTCCACACAACCACGAGTTGCTCATCTCTCCACCCAATCATCACTAG.
      ||  |||   |   ||  ||     ||    |    ||      || ||    |   ||
-233 CTGACCTCTACCGACCGGACTTGAATGCGCTACCTTCGTCAGCGACGATGGCCGCGTACG

................................................

-173 CTGGCGACGTGCCCCCGCATGCATGGCGGCACATGGCGAGCTCAGACCGTGCGTGGCTGG

-40  ...........................................CTAATACGGTGCACTGTTAGCTA
                                                 ||  |  ||       |||||  ||
-113 CTACAAATACGTACCCCGTGAGTGCCCTAGCTAGAAACTTACACCTGCAACTGCGAGAGC
```

FIG. 4(b)-2

```
              *
-17  CAGACCAAGAAGTGATCATG
     ||      ||  |||
-53  GAGCGTGTGA.GTGTAGCCGAGTAGATCACCGTACGACGACGACGAGGGGCATG
```

FIG. 5(a) p687LtpW1-GUS
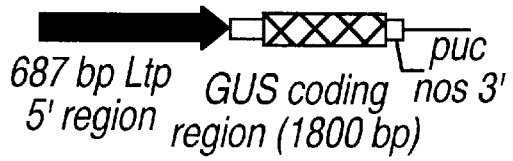
687 bp Ltp 5' region | GUS coding region (1800 bp) | puc nos 3'
FIG. 5(b) p473LtpW1-GUS
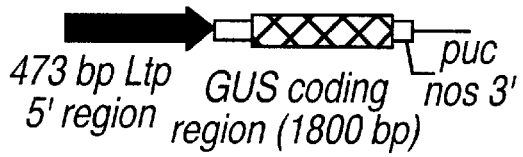
473 bp Ltp 5' region | GUS coding region (1800 bp) | puc nos 3'
FIG. 5(c) p206LtpW1-GUS
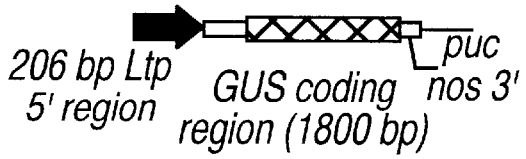
206 bp Ltp 5' region | GUS coding region (1800 bp) | puc nos 3'
In all three constructs, the ADH1S6 intron lies between The LtpW1 promoter and the GUS coding region.
FIG. 5(d) pLC-GUS
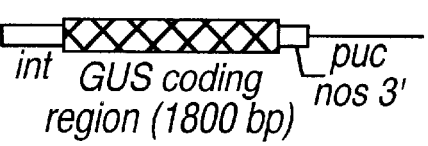
Sma1 — int — GUS coding region (1800 bp) — puc nos 3' p35S-GUS

The ADH1S intron lies between the promoter and the GUS gene pAct-GUS

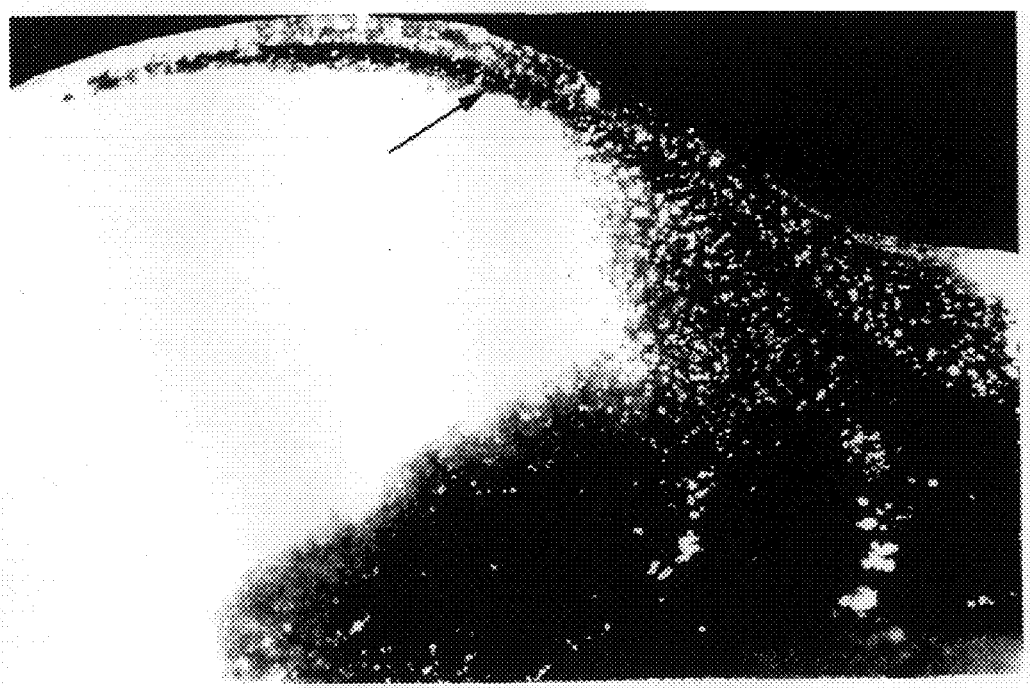

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 687 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: LtpW1

(ix) FEATURE:
        (A) NAME/KEY: regulatory element
        (B) LOCATION:1..687

(xi) SEQUENCE DESCRIPTION: SEQ ID NO: 1:

```
CTAGAGAAAG AGTTTTAGAC CGGAGGTATT TGTTAGGAAG TACTTCTTGC CATACTAGTT      60

TCAATAAAGT AGCTTGAAAA GACATTTGTT AAGCAACCAT GTGTTTTTAA TATGAAGATC     120

CTCAATACCG AGAGCCTTTG GTCCCATGGA TGACACAAAA CTTCCCACTT GTTTTTTTTT     180

TTTGTGTGTG TGTGGGTAAA CTTCCCACTT GGTTAACCTA TACTTCCGCT TATGTTCATC     240

ACTTTGCCAG AAAATTGCAT ATGTGAAGGA AGTGCCAATA TTTAATACCG TCTGGTGTTA     300

TAAATTCATC TCCCAAAATT ATTGGAGTTG AAGATTCACT TGAAAAAATA ATTTGACATA     360

TTAAAGATGT TGCCCTTGCG CGGGGTATCT GCAAATTGAG GATCCAAGGG ACGATTGCAT     420

CCAGTTCTAA ACACACCATT ATGATTTCAG TGATAATGCA TGCTTCCAAA GCCCAGCTGC     480

AAGCTTGGGC CATCCTTCGG AAGGGAAAAA GAAAAAGGGG TCCTGCTGCA CCAGCGACTA     540

AACCATCCAC GCATCTCTCG CTCGAACCCC TATTTAAGCC CCTCCATTCT TCCCTACATT     600

CTCCACACAA CCACGAGTTG CTCATCTCTC CACCCAATCA TCACTAGCTA ATACGGTGCA     660

CTGTTAGCTA CAGACCAAGA AGTGATC                                        687
```

(2) INFORMATION FOR SEQ ID NO: 2:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: LtpW1

```
    (ix) FEATURE:
         (A) NAME/KEY: regulatory element
         (B) LOCATION:1..473

(xi) SEQUENCE DESCRIPTION: SEQ ID NO: 2:

AACCTATACT TCCGCTTATG TTCATCACTT TGCCAGAAAA TTGCATATGT GAAGGAAGTG     60

CCAATATTTA ATACCGTCTG GTGTTATAAA TTCATCTCCC AAAATTATTG GAGTTGAAGA    120

TTCACTTGAA AAAATAATTT GACATATTAA AGATGTTGCC CTTGCGCGGG GTATCTGCAA    180

ATTGAGGATC CAAGGGACGA TTGCATCCAG TTCTAAACAC ACCATTATGA TTTCAGTGAT    240

AATGCATGCT TCCAAAGCCC AGCTGCAAGC TTGGGCCATC CTTCGGAAGG GAAAAAGAAA    300

AAGGGGTCCT GCTGCACCAG CGACTAAACC ATCCACGCAT CTCTCGCTCG AACCCCTATT    360

TAAGCCCCTC CATTCTTCCC TACATTCTCC ACACAACCAC GAGTTGCTCA TCTCTCCACC    420

CAATCATCAC TAGCTAATAC GGTGCACTGT TAGCTACAGA CCAAGAAGTG ATC          473

(2) INFORMATION FOR SEQ ID NO: 3:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
         (B) CLONE: LtpW1

(ix) FEATURE:
         (A) NAME/KEY: regulatory element
         (B) LOCATION:1..206

(xi) SEQUENCE DESCRIPTION: SEQ ID NO: 3:

AGCTTGGGCC ATCCTTCGGA AGGGAAAAAG AAAAAGGGGT CCTGCTGCAC CAGCGACTAA     60

ACCATCCACG CATCTCTCGC TCGAACCCCT ATTTAAGCCC CTCCATTCTT CCCTACATTC    120

TCCACACAAC CACGAGTTGC TCATCTCTCC ACCCAATCAT CACTAGCTAA TACGGTGCAC    180

TGTTAGCTAC AGACCAAGAA GTGATC                                         206

(2) INFORMATION FOR SEQ ID NO: 4:

(i) SEQUENCE CHARACTERISTICS:
        (A) LENGTH: 1469 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
         (B) CLONE: LtpW1

(ix) FEATURE:
         (A) NAME/KEY: regulatory element
         (B) LOCATION:1..687

(xi) SEQUENCE DESCRIPTION: SEQ ID NO: 4:

TCTAGAGAAA GAGTTTTAGA CCGGAGGTAT TTGTTAGGAA GTACTTCTTG CCATACTAGT     60

TTCAATAAAG TAGCTTGAAA AGACATTTGT TAAGCAACCA TGTGTTTTTA ATATGAAGAT    120

CCTCAATACC GAGAGCCTTT GGTCCCATGG ATGACACAAA ACTTCCCACT TGTTTTTTTT    180

TTTTGTGTGT GTGTGGGTAA ACTTCCCACT TGGTTAACCT ATACTTCCGC TTATGTTCAT    240

CACTTTGCCA GAAAATTGCA TATGTGAAGG AAGTGCCAAT ATTTAATACC GTCTGGTGTT    300
```

-continued

```
ATAAATTCAT CTCCCAAAAT TATTGGAGTT GAAGATTCAC TTGAAAAAAT AATTTGACAT      360

ATTAAAGATG TTGCCCTTGC GCGGGGTATC TGCAAATTGA GGATCCAAGG GACGATTGCA      420

TCCAGTTCTA AACACACCAT TATGATTTCA GTGATAATGC ATGCTTCCAA AGCCCAGCTG      480

CAAGCTTGGG CCATCCTTCG GAAGGGAAAA AGAAAAAGGG GTCCTGCTGC ACCAGCGACT      540

AAACCATCCA CGCATCTCTC GCTCGAACCC CTATTTAAGC CCCTCCATTC TTCCCTACAT      600

TCTCCACACA ACCACGAGTT GCTCATCTCT CCACCCAATC ATCACTAGCT AATACGGTGC      660

ACTGTTAGCT ACAGACCAAG AAGTGATCAT GGCCCGCGCT CAGGTAATGC TCATGGCCGT      720

CGCCTTGGTG CTCATGCTCG CGGCGGTCCC GCGCGCTGCC GTGGCCATCG ACTGCGGCCA      780

CGTTGACAGC TTGGTGAGAC CCTGCCTGAG CTACGTTCAG GGCGGCCCCG GCCCGTCTGG      840

GCAGTGCTGC GACGGCGTCA AGAACCTCCA TAACCAGGCG CGATCCCAGA GCGATCGCCA      900

AAGCGCTTGC AACTGCCTCA AGGGGATCGC TCGTGGCATC CACAATCTCA ACGAGGACAA      960

CGCCCGCAGC ATCCCCCCCA AGTGCGGTGT CAACCTCCCA TACACCATCA GTCTCAACAT     1020

CGACTGCAGC AGGTGATTAA TTCACATGCA AGCATATATA TATGAACACT CATCCACGTA     1080

AAATTTATTG ATATTAACAT TAATCAAATC TTTGCACTGC AGGGTGTAAT GGGCGACGAT     1140

CCGTCAAGCT GGTGCTCAGC TCATCCATCC ACGTGGAGTT GAAGCGCGCA GCCTCTATCC     1200

CTATGTAGTA TGGTCACTAG TTATGCGAGT TTATACTGAA TATGAATAAG AACTCTCTCC     1260

AGCTGGCTTG CTGGTACTCC TCTGGAGGAG ATCAGTATCT GTGTACCTGA GAGTTGAGAG     1320

TTTGTACCAT GGGCACTCCC AGTGTTTATG GACTTTAATA CATACAACTC GTTCTGTTCA     1380

GCGTGTGACT TATCTTTGTT TCCTCACGTT CGCCTGTCAT ATACTCCTTC CATCCGGTAT     1440

TAGTTGGCGT TCAAACGGAT ATATCTAGA                                       1469
```

WHEAT ALEURONE REGULATORY REGION

This application is a Continuation-in-part of U.S. application Ser. No. 09/102,046 filed Jun. 22, 1998 now U.S. Pat. No. 6,013,862.

BACKGROUND OF THE INVENTION

The present invention relates to plant gene regulatory regions and their use in the expression of genes of interest. More specifically, the present invention relates to the use of an aleurone regulatory region for organ, and tissue specific expression of a gene of interest within aleurone tissues of plants, and for constitutive expression of a gene of interest within monocot and dicotyledonous plants.

The endosperm of a seed is the site of deposition of storage products such as starch and proteins used by the developing embryo during germination. The endosperm surrounds the embryo of developing and mature cereal seeds. The endosperm comprises a peripheral layer of aleurone cells, which are specialized secretory cells. During germination, the aleurone layer is involved in the transfer of metabolites from the transport system to the endosperm. Furthermore, several antimicrobial compounds required to protect the seed during dormancy, imbibition and germination are synthesized within this tissue. The aleurone cells differentiate from primary endosperm cells 10–21 days after fertilization.

Several aspects of hormonal regulation of gene transcription within aleurone tissue, in germinating barley seeds have been well characterized (Fincher 1989, Annu. Rev. Plant Physiol. Mol. Biol. 40:305–346). For example, genes encoding α-amylase, responsible for the digestion of the starch stored within the starchy endosperm, and β-glucanase, which digests the cell walls, have been isolated and characterized (WO 90/01551 Rogers; U.S. Pat. No. 5,677,474 Rogers, issued Oct. 14, 1997; Karrer et al 1991, Plant Mol. Biol. 16:797–805; Slakeski and Fincher 1992). Furthermore, several structural and regulatory genes involved in anthocyanin biosynthesis within the aleurone have been isolated and characterized (Paz-Ares et al 1987, EMBO J. 5:829–833; Dellaporta et al 1988, pp263–282 18th Stadler Genet. Symp. ed. J. P. Gustafsant and R. Appels). Other genes representing differentially expressed transcripts within aleurone layers have also been reported including CHI26 (Lea et al 1991, J. Biol. Chem. 266:1564–73); pZE40 (Smith et al 1992, Plant Mol. Biol. 20:255–66); pHvGS-1, and pcHth3 (Heck and Ho 1996, Plant Mol. Biol. 30:611–23). Several genes encoding lipid transfer proteins (Ltp) have also been obtained from barley aleurone tissues, including B11E-barley Ltp1, and B12A-barley Ltp2 (Jakobsen et al 1989, Plant Mol. Biol. 12: 285–93). Only one of these genes, B12A, has been expressed ectopically in transgenic plants. In this case the promoter is active only during seed development (Kalla et al 1994 Plant J. 6:849–860)

Lipid transfer proteins are responsible for the transfer of phospholipids between membranes in vitro, and likely play a role during membrane biogenesis. This may be especially important in aleurone cells which are known to develop extensive membrane systems. Skriver et al (1992, Plant Mol. Biol. 18: 585–589) disclose the sequence of a genomic Ltp (Ltp1), including the promoter region, from barley. Northern analysis demonstrated that this gene was specifically expressed in developing and germinaring seeds, as well as in whole seeds and aleurone layers obtained from seeds 30 days post anthesis (dpa). No expression of Ltp1 mRNA was observed in root, leaf, or shoot tissues, or coleoptiles of germinating seeds. Linnestad et al (1991, Plant Physiol 97: 841–843) also discloses the promoter sequence of the Ltp1 promoter from barley which was obtained using barley cDNA B12A as a probe. The Ltp1 promoter, as well as a modified form of this promoter is disclosed in WO 95/23230 (Feb. 23, 1995; Olsen et al). The modified form of the Ltp1 promoter was not specific to directing expression within aleurone cells, and was active in a range of plant organs and tissues including aleurone cells, scutellar epithelial tissue and vascular tissue during germination or in the plant, including root, leaves and stem.

The promoter of B12A (also termed Ltp2) directs expression specifically within the aleurone layer of developing grain as determined using transgenic cereal plants (Kalla et al 1994, Plant J. 6: 849–860). The sequence of the Ltp2 promoter is disclosed in CA 2,110,772 (filed Dec. 6, 1993, Olsen and Kalla) and U.S. Pat. No. 5,525,716 (Kalla et al). Dieryck et al (1992, Plt,. Molec. Biol 19:707–709) disclose the incomplete CDNA sequence of a wheat (*Triticum durum*) Ltp (pTd4.90). Ltp genes comprise a multigenic family and are ubiquitous in plants. Unfortunately as these genes or corresponding proteins have been isolated from various species there is no uniformity in the terminology used to identify the genes. Hence Ltp1 from tobacco, barley and Arabidopsis are not the same. As well, two barley Ltp2 genes are described in the literature; barley Lpt2 as described in Molina and Garcia-Olmedo (Plant J. 4:983–991) is a leaf Lpt, while barley Ltp2 as described in Kalla et al (1994 Plant J. 6:849–860) is aleurone specific.

It is desirable to provide regulatory regions capable of controlling aleurone specific expression that is not detrimental to the developing embryo and seedling. Aleurone-specific regulatory regions may be used for the regulation of the expression of heterologous or native genes within aleurone tissue of cereal seeds in order to modify grain development and germination. For example, placing genes of interest under the control of aleurone-specific regulatory regions may be used to:

1) mediate the unloading of metabolites from the transport system into the endosperm, since this metabolite unloading is processed through aleurone cells. By expressing genes of interest involved in tis process specifically within the aleurone, the grain yield may be affected. For example, which is not to be considered limiting in any manner, these genes of interest may include $Na^+$ and $K^+$ ATPases functioning in active transport, modifiers of membrane pore exclusion parameters such as TMV movement proteins, invertase for sucrose transport etc.;

2) affect the quality of the grain, through the production of specific proteins or enzymes, lipids, secondary metabolizes etc. and their secretion into the endosperm during endosperm development or endosperm digestion. For example, which is not to be considered limiting in any manner, such proteins may include starch syntheses, ADP glucose pyrophosphorylase, monoclonal antibodies, glutenins, anticoagulants (eg hirudin), anti-pathogenic phenolics etc. Furthermore, expression of a gene of interest within the aleurone may also be used in order to express proteins for nutritional or medicinal purposes for feeding to animals or humans;

3) regulate pre-harvest sprouting by affecting dormancy, for example which is not to be considered limiting, by over-expression of ACC syntheses to induce inhibitory levels of ethylene;

4) enhance alcohol production—introduction of novel high temperature resistant enzymes for industrial application, including, but not limited to, thermostable amylases, pectinases and invertase;

5) modify disease resistance of developing and germinating grains by expressing proteins, for example but not limited to, oxalate oxidase, glucose oxidase, chitinase, or lipid transfer proteins, in combination with a suitable signal peptide for targeting to the extracellular matrix and cell wall localization. This approach can be used to modify the matrix to provide a stronger physical barrier against invading pathogens or to direct specific anti-pathogen agents to the aleurone/pericarp interface.

This invention characterizes a novel wheat aleurone specific regulatory region active during embryo development and germination and which controls expression of heterologous genes of interest within transgenic plants. Furthermore, this invention relates to a constitutive regulatory element that is active within monocot and dicotyledonous plants, and which can be used to drive the expression of a gene of interest in a variety of plants.

SUMMARY OF THE INVENTION

The present invention relates to plant gene regulatory regions and their use in the expression of genes of interest. More specifically, the present invention relates to the use of a constitutive regulatory region for expression of a gene of interest within both monocotyledonous and dicotyledonous plants.

Accordingly, the present invention is directed to a chimeric regulatory element comprising:

i) a first regulatory element comprising the nucleotide sequence of SEQ ID NO:3, or a nuclectide sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., and exhibits regulatory element activity; and ii) a second regulatory element comprising at least one exogenous mediator of the regulatory activity of the first regulatory element.

The present invention also pertains to the chimeric regulatory element as defined above wherein the second regulatory element is an enhancer element, or a silencer element.

This invention embraces a vector, or an expression vector comprising the chimeric regulatory element as defined above in operative association with a gene of interest, and a transformed plant cell culture, or a transformed plant comprising this vector. The transgenic plant may be either a monocotyledonous plant or a dicotyledonous plant.

This invention also relates to a transgenic dicotyledonous plant comprising a gene construct comprising:

i) the nucleotide sequence of SEQ ID NO:3 or a nucpeotide sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., wherein the nucleotide sequence exhibits regulatory element activity; and ii) a gene of interest in operative association with the nucleotide sequence.

Furthermore, the present invention is directed to a method of expressing a gene of interest within a plant comprising:

i) a gene of interest for which expression is desired in operative association with the chimeric regulatory region comprising a first regulatory element comprising the nucleotide sequence of SEQ ID NO:3, or a nucleotide sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., and exhibits regulatory element activity; and a second regulatory element comprising at least one exogenous mediator of the regulatory activity of the first regulatory element to produce a gene construct; and ii) introducing the gene construct into the plant and allowing for expression of the gene of interest.

This method may be performed using either a monocotyledonous, or a dicotyledonous plant.

This invention also pertains to a method of expressing a gene of interest within a dicotyledonous plant comprising:

i) a gene of interest for which expression is desired in operative association with the nucleotide sequence of SEQ ID NO:3 or a nucleotide sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., wherein the nucleotide sequence exhibits regulatory element activity, to produce a gene construct; and ii) introducing the gene construct into the dicotyledonous plant and allowing for expression of the gene of interest.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1(a) shows *Hordeum vulgate* at 20 dpa; FIG. 1(b) shows *Triticum aestivurn* at 10 dpa; FIG. 1(c) shows *T. aestivum* at 20 dpa; FIG. 1(d) shows *T. tungidum* at 10 dpa.

FIG. 2 shows RNA in situ hybridization of $^{35}$S-labelled barley Ltp ribo-probe in 73h germinating, and 18 dpa developing wheat grain. FIG. 2(a) and FIG. 2(c) show hybridization results using anti-sense probe; FIG. 2(b) and FIG. 2(d) show hybridization with sense probe.

FIG. 3 shows the DNA sequence of the genomic LtpW1 gene. The coding region is underlined (the intron is not underlined). The ATG start and TGG stop codon are in bold type. The cap site, TATA, CAT boxes are italicized and double-underlined at positions −83, −117 and −222, respectively. SEQ ID NO 1 runs from −687 to −1, SEQ ID NO 2 runs from −473 to −1, and SEQ ID NO 3 runs from −206 to −1.

FIG. 4 shows the DNA sequence alignment of LtpW1 and barley Ltp genes. FIG. 4(a) shows alignment of LtpW1 (top row) and barley Ltp1 (bottom row); FIG. 4(b) shows alignment of LtpW1 (top row) and barley Ltp2 (Kalla et al 1994 Plant J. 6:849–860). The ATG of the Ltp genes is overlined.

FIG. 5 shows the LtpW1 regulatory region constructs, in all three constructs the ADH1S6 intron lies between the LtpW1 regulatory region and the coding region of the marker gene, GUS. FIG. 5(a) p687LtpW1-GUS; FIG. 5(b) p473LtpW1-GUS; FIG. 5(c) p206LtpW1-GUS; FIG. 5(d) pLC-GUS, the promoterless control used in transient assays.

FIG. 5(b) shows Zea mays at 13 dpa.

FIG. 8 shows GUS expression in aleurone layer (arrowed) of 3 days germinated kernel of Z. mays, T1 self progeny, transformed with p473LtpW1-GUS fusion.

CK44 is a non-transformed control, and Act-oxo Homo is an actin-OXO $T_5$ line homozygous for the OXO gene, and is a high expressing positive control. The remaining $T_0$ transgenic lines comprise p206Ltp-oxo.

DESCRIPTION OF PREFERRED EMBODIMENT

The present invention relates to plant gene regulatory regions and their use in expression of genes of interest. More specifically, the present invention relates to the use of a constitutive regulatory region for expression of a gene of interest within plants.

The following description is of a preferred embodiment by way of example only and without limitation to the combination of features necessary for carrying the invention into effect.

Described below is a constitutive regulatory element p206LtpW1 (SEQ ID NO:3), that is active in both monocotyledonous and dicotyledonous plants. The constitutive regulatory element was obtained from a wheat genomic Ltp sequence termed LtpW1 (SEQ ID NO:4). The coding region of the LtpW1 gene sequence exhibits about an 85% homology with barley Ltp1, and includes a 26 amino acid transit peptide. The regulatory region of a wheat lipid transfer protein (Ltp) gene, LtpW1, has been isolated and characterized. This regulatory region comprises a novel oligonucleotide sequence (SEQ ID NO: 1), which is active in aleurone of wheat, maize and barley. The full length regulatory region is not active in leaf, root, or coleoptile tissues. However, a truncated form of LtpW1 regulatory region, termed 206Ltp or 206LtpW1 (SEQ ID NO 3), is active in a range of tissues and plant organs, and is active in both monocot and dicot plants.

The regulatory region region of LtpW1 compared to the barley Ltp1 regulatory region has 43% sequence similarity with the majority of sequence similarity (82%) occurring within 140 nucleotides upstream of the transcriptional start site (see FIG. 4(a)). A minor sequence similarity was noted between LtpW1 and a barley amylase protease inhibitor, however, no sequence similarity of any significance was observed between LtpW1 and Ltp2, or other known Ltp regulatory region sequences.

The full length LtpW1 regulatory region (687 nucleotides; p687LtpW1; SEQ ID NO:1), or a truncated LtpW1 regulatory region, p473LtpW1 (SEQ ID NO:2; comprising a 473 nucleotide fragment of the full length regulatory region or bps 214–687 of SEQ ID NO:1), can be used to drive the expression of a gene of interest within the aleurone layer of a developing and germinating seed of a monocotyledonous plant, for example, but not limited to, wheat, rice, barley and maize.

Figure 7A:
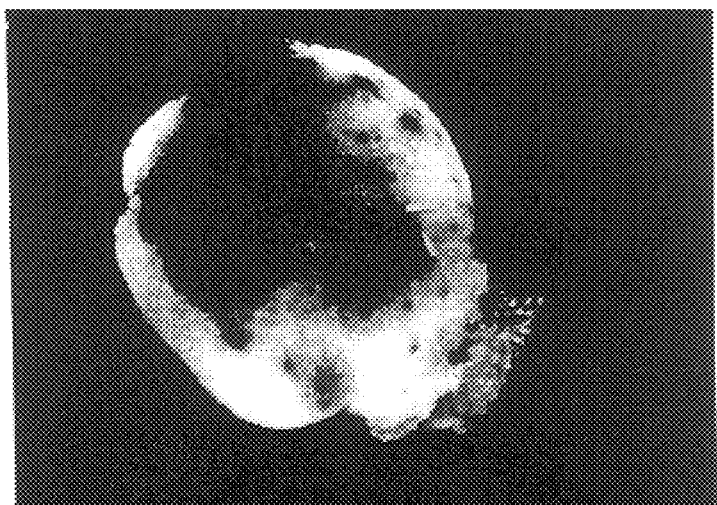
FIG. 7(a) shows T. aestivum at 15 dpa.
Figure 7B:
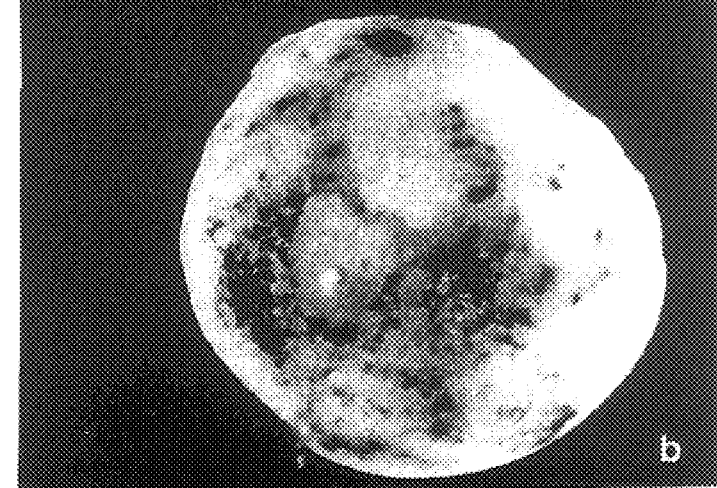
FIG. 7 shows transient expression of LtpW1 regulatory region—GUS (p687LtpW1-GUS) fusion in aleurone of cereal grains delivered by microprojectile bombardment.
FIG. 7(c) shows H. vulgare at 12 dpa.
Figure 7C:
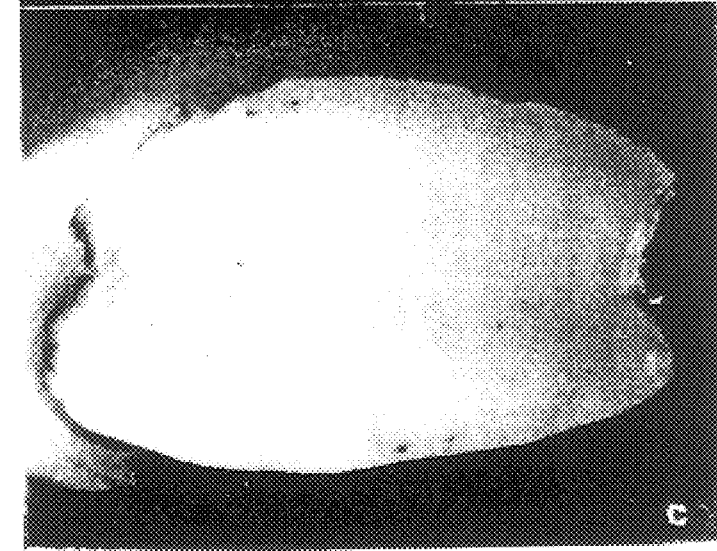
Figure 9:
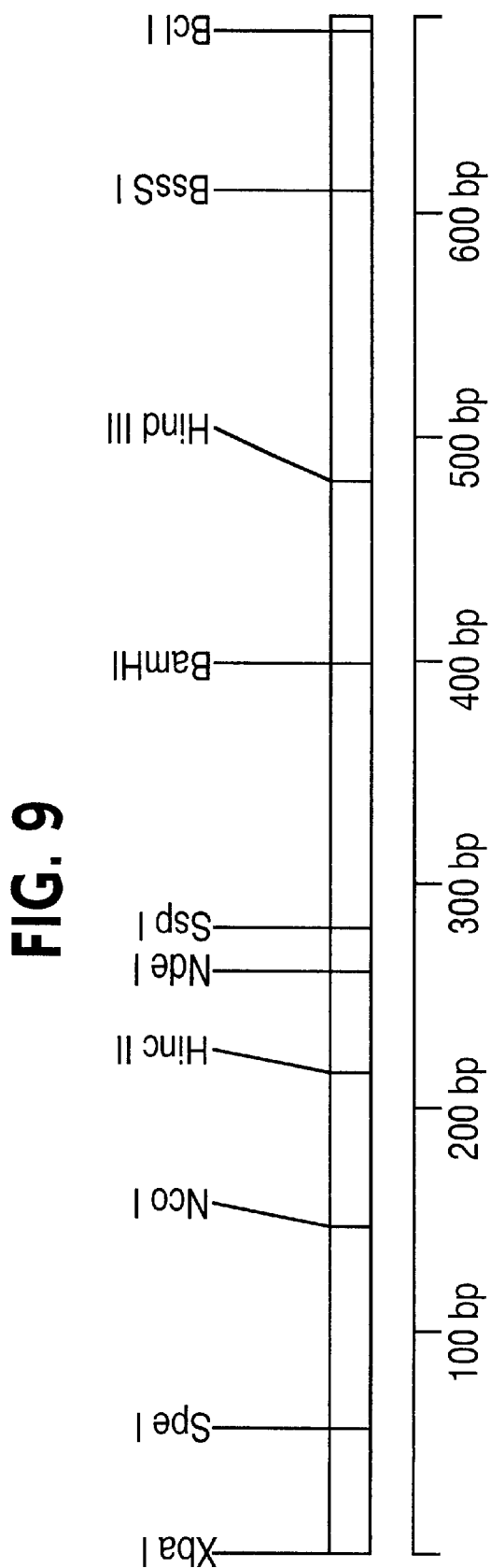
FIG. 9 shows a restriction map of the LtpW1 regulatory region region corresponding to the sequence of SEQ ID NO:1.

LTpW1 exhibits 8.8% of 35S activity and 12.2% activity of the strong rice action monocot constitutive regulatory region (Table 2, Example 3). Comparison of histological evidence of expression of Ltp2 (Kalla et al 1994, Plant J. 6.849–860)), with FIG. 7 of the present invention (histological evidence of LtpW1 activity) indicates that LtpW1 is more than two times stronger than Ltp2.

Experiments with deletions of the LtpW1 regulatory region indicate that the 473 nucleotide fragment (SEQ ID NO: 2; p473LtpW1) or bps 214–687 of SEQ ID NO:1 of the full length regulatory region is more active in aleurone tissue than the 687 base pair regulatory region, (SEQ ID NO: 1), p687LtpW1 (Table 3). However, neither the full length regulatory region, nor the 473 bp truncated regulatory region (p473LtpW1) were active in leaf tissue (see Table 4). A truncated regulatory region comprising a 206 bp nucleotide fragment (SEQ ID NO:3, p206LtpW1, bps 481–687 of SEQ ID NO:1) of the full length regulatory region was active in aleurone, leaf, and scutellum tissue, functioning as a minimal regulatory region element. This 206 bp region therefore represents a novel, constitutive, regulatory region useful for expressing a gene of interest within plants.

The 206 bp region was also found to direct the expression of a gene of interest within leaf tissue of a range of dicotyledonous planus, including Soya, Brassica and Nicotiana (Table 6, Example 6). Chimeric constructs comprising the strong monocot promoter, the rice actin promoter (McElroy D., Zhang, W., Cao, J., and Wu, R. 1990. Plant Cell 2:163–171) were also introduced into these plants, and no activity was observed. These results indicate that the 206 bp region also represents a novel constitutive regulatory region active in a range of plants, including both dicotyledonous and monocotyledonous plants.

FIG. 3 shows the sequence of the LtpW1 gene comprising the regulatory element region as identified in SEQ ID NO:1. The numbering of the regulatory region in FIG. 3 is from base pairs –687 to –1, while the coding region of the gene is from base pairs +1 to 753. Therefore, p687LtpW1 comprises the sequence of SEQ ID NO:1 (nucleotides 1–687), which are equivalent to the sequence of base pairs –687 to –1 of FIG. 3. p473LtpW1 comprises the sequence of SEQ ID NO:2, nucleotides 214–687 of SEQ ID NO:1, or bps –473 to –1 of FIG. 3. p206LtpW1 comprises the sequence of SEQ ID NO:3, nucleotides 481–687 of SEQ ID NO:1, or bps –206 to –1 of FIG. 3.

By "regulatory element" or "regulatory region", it is meant a portion of nucleic acid typically, but not always, upstream of a gene, and may be comprised of either DNA or RNA, or both DNA and RNA. The regulatory elements of the present invention includes those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. It is also to be understood that enhancer elements may be repeated thereby further increasing the enhancing effect of an enhancer element on a regulatory region. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular size is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute lo the regulation of expression of a coding region of interest. A regulatory element may also include those elements located downstream (3') to the size of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, of the present invention may be operatively associated with heterologous or exogenous regulatory elements or promoters in order to modulate or mediate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the present invention may be operatively associated with enhancer or silencer elements, to mediate the activity of such regulatory elements within a variety of plants. Furthermore, an intron, for example, but not limited to, the IVS6 intron from maize (Callis, J., 1987, Genes Dev. 1: 1183–1200). or the maize actin intron (McElroy, D. et al., 1991. Mol. Gen. Genet. 231: 150–160), may be included for optimizing expression within monocotyledonous plants.

An "analogue" of the regulatory elements described herein include any substitution, deletion, or additions to the sequence of a regulatory element provided that said analogue maintains at least one regulatory property associated with the activity of the regulatory element. Such properties include directing organ specificity, tissue specificity, or a combination thereof, or temporal activity, or developmental activity, or a combination thereof, or other regulatory attributes including, constitutive activity, negative regulatory elements, enhancer sequences, or sequences that affect stability of the transcription or translation complexes or stability of the transcript.

The DNA sequences of the present invention thus include the DNA sequences of SEQ ID NO: 1, 2, and 3, the regulatory regions and fragments thereof, as well as analogues of, or nucleic acid sequences comprising about 80% similarity with the nucleic acids as defined in SEQ ID NO's: 1, 2 or 3. Analogues (as defined above), include Nhose DNA sequences which hybridize under stringent hybridization conditions (see Maniatis er al., in Molecular Cloning (A Laboratory Manual), Cold Spring Harbor Laboratory, 1982, p. 387–389) to any one of the DNA sequence of SEQ ID NO: 1, 2, or 3 provided that said sequences maintain at least one regulatory property of the activity of the regulatory element as defined herein.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 5×SSC at 42° C. and washing in from about 0.5×SSC to about 0.2×SSC at 65° C. Analogues include chose DNA sequences which hybridize to any one of the sequences of SEQ ID NO: 1, 2 or 3 under these hybridization conditions.

A constitutive regulatory element directs the expression of a gene throughout the various pans of a plant and continuously throughout plant development. Examples of known constitutive regulatory elements include promoters associated with the CaMV 35S transcript. (Odell et al., 1985, *Nature*, 313: 810–812), the rice actin 1 (Zhang et al, 1991, *Plant Cell*, 3: 1155–1165) and triosephosphate isomerase 1 (Xu et al, 1994, *Plant Physiol.* 106: 459–467) genes, the maize ubiquitin 1 gene (Cornejo et al, 1993, *Plant Mol. Biol.* 29: 637–646), the Arabidopsis ubiquitin 1 and 6 genes (Holtorf et al, 1995, *Plant Mol. Biol.* 29: 637–646), and the tobacco translational initiation factor 4A gene (Mandel et al, 1995 *Plant Mol. Biol.* 29: 995–1004). The regulatory element, p206LtpW1, as described herein, is another example of a constitutive regulatory element.

The present invention pertains to a chimeric regulatory region comprising the p206Ltp regulatory region as defined by SEQ ID NO:3, or a nucleic acid that hybridizes to SEQ ID NO:3, as defined above, and one or mediators of this regulatory activity. By "mediate", it is meant the activity associated with an exogenous regulatory element that further regulates the activity of p206Ltp. For example, which is not to be considered limiting in any manner, a mediator may either up regulate, down regulate the activity of p206Ltp, and comprise one or more enhancer or silencer elements, respectively. Examples of enhancer elements are known in the art, and include, but are not limited to, enhancers active in dicotyledonous and monocotyledonous plans, the 35S enhancer, actin enhancer, and me enhancer from T1275 (U.S. Pat. No. 5,824,872, which is incorporated herein by reference).

Nucleic acid constructs comprising a chimeric regulatory region associated with 206LtpW1 were therefore examined to determine if exogenous regulatory regions, mediators, may further regulate the activity of 206LtpW1. Transient expression assays indicate that an enhancer element obtained from tobacco is active in increasing the activity of 206LtpW1 in plants (Table 6, Example 6). Therefore, the present invention is also directed to gene constructs comprising the 206LtpW1 regulatory region associated with at least one other exogenous regulatory region, and in operative association with a gene of interest.

Any exogenous gene, or gene of interest, can be used and manipulated according to the present invention to result in the expression of the exogenous gene.

By "gene of interest" it is meant any gene that is to be expressed within a host organism. Such a gene of interest may include, but is not limited to, a gene that encodes a protein directed at improving an agronomic trait of the plant, for example but not limited to improving plant defense against pathogens, or resistance to herbicides. A gene of interest may also include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, intereons, for example, interferon-α, interferon-β, interferon-π, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobactenum rumor inducing (Ti) plasmid genes, such as the nopaline syntheses (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation ot the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be farther manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

The data presented herein indicate that nucleotides 1–214 and 215–481 of SEQ ID NO: 1 (–687 to –473, and –472 to –206 of FIG. 3, respectively) are responsible for imparting tissue specificity within this regulatory region, since once the nucleotides 1–481 (–687 to –206 of FIG. 3) are removed from the full length regulatory region, tissue specificity is lost (Table 4). It is contemplated that either of these regions may be combined with any suitable regulatory region of interest, for example, which is not to be considered limiting, a minimal, constitutive, or viral promoter etc. In order to obtain aleurone-specific expression of a gene linked thereto. Both of these regions were found to comprise very low sequence similarity with other sequences present within gene sequence databases such as GenBank.

Furthermore, the data presented in Table 3 indicates that the region comprising nucleotides 1–481 of SEQ ID NO: 1 (–687 to –206 of FIG. 3) is responsible for regulating the strength of regulatory region activity, and includes both silencer- and enhancer-type activities. For example, the fragment comprising nucleotides 215–481 of SEQ ID NO: 1 (–473 to –206 of FIG. 3) may be used as an enhancer like element as constructs comprising this region (e.g. p473LtpW1) resulted in increased expression when compared with either the full length regulatory region (p687LtpW1) or the truncated regulatory region p206LtpW1 (see Table 3). Similarly, nucleotides 481–687 of SEQ ID NO: 1 (–206 to –1, of FIG. 3) also exhibit enhancer-type activity, since constructs comprising this region (p206LtpW1) exhibited higher levels of expression than the full length regulatory region. Therefore, it is contemplated that nucleotides 214–481, or 481–687 (–473 to –206, and –206 to –1 of FIG. 3, respectively) may be combined with any suitable regulatory region of interest, for example, which is not to be considered limiting, a minimal, constitutive, or viral promoter etc., in order to obtain both aleurone-specific expression of a gene linked thereto, as well as increased gene expression.

Similarly, the fragment comprising nucleotides 1–214 (of SEQ ID NO:1, or –687 to –473 of FIG. 3) comprises silencer-type elements as constructs comprising this region (e.g. p687LtpW1) result in lower levels of expression compared with the levels of expression obtained with either of the truncated regulatory region constructs, p206LtpW1, or p473LtpW1 (see Table 3). It is contemplated that nucleotides 1–214 (of SEQ ID NO:1, or –687 to –473 of FIG. 3) may be combined with any suitable regulatory region of interest, for example, which is not to be considered limiting, a minimal, constitutive, or viral promoter etc., in order to obtain both aleurone-specific expression of a gene linked thereto, along with reduced gene expression.

The truncated regulatory region, p473LtpW1, was used to transform maize, where it was noted that this regulatory region was active only in aleurone of developing and germinating cereal grain.

In transient assays, activity of the 206 bp HinII/BcII truncated regulatory element (SEQ ID NO3; FIG. 3) in non-aleurone tissues was relatively low (7–11%) compared to other constitutive promoters (see Table 4, Example 3). However, the level of stable expression in transformed plants (FIG. 10) was high, equalling the activity observed for the expression of a gene of interest under the control of a strong monocot regulatory element, the rice actin promoter (McElroy D., Zhang, W., Cao, J., and Wu, R. 1990. Plant Cell 2:163–171).

The gene constructs of the present invention can also include other optional regulatory motifs such as enhancers, either translation or transcription enhancers, as may be required. These enhancer regions are well known to persons skilled in the art, and can include, for example, the enhancer region of the 35S regulatory region, as well as other enhancers obtained from other regulatory regions, and/or the ATG initiation codon and adjacent sequences. The initiation codon must be in phase With the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

Also considered part of his invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, embryo or shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. DT. Dennis, DH Turpin, DD Lefebrve, DB Layzell (eds), Addison Wesly, Langmans Ltd. London, pp. 561–579 (1997). The present invention further includes a suitable vector comprising the chimeric gene construct.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLE 1

Localization of Ltp1 Expression

Figure 1:
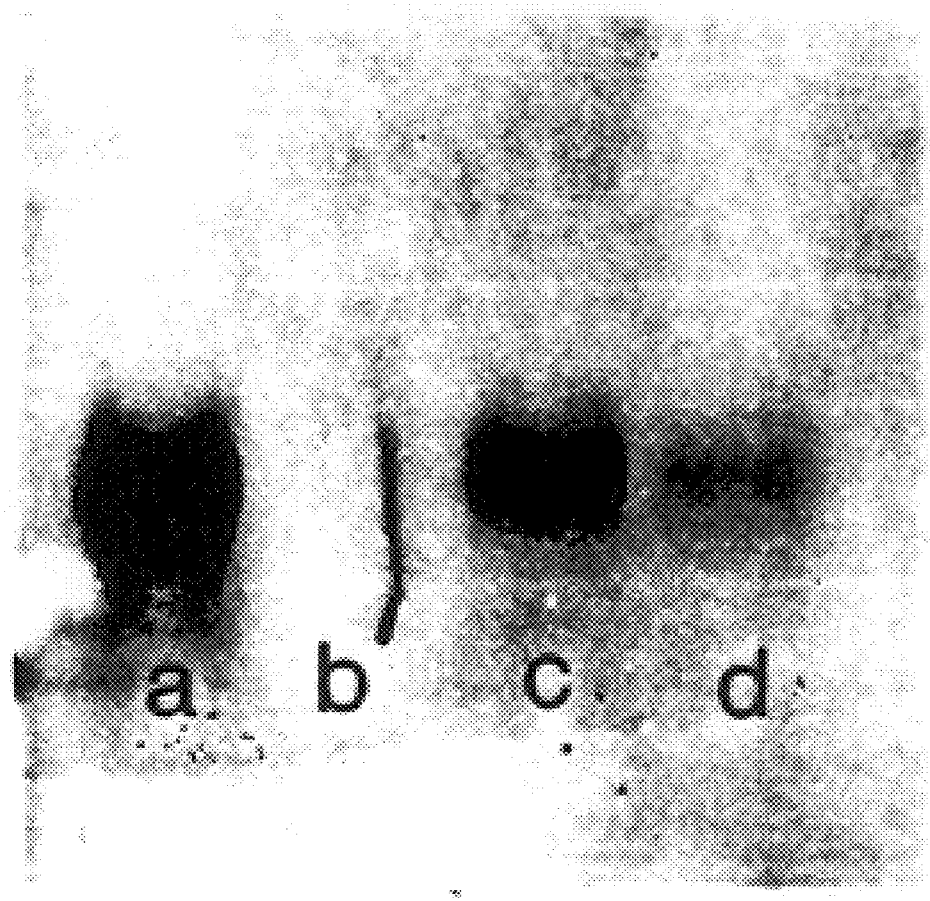
FIG. 1 shows Ltp expression in aleurone tissues of Hordeum and Triticum species using Northern analysis hybridized with a barley Ltp1 DIG-labelled CDNA.

In order to isolate genes which are functional in aleurone of developing and germinating wheat grain, a barley cDNA probe of an aleurone specific lipid transfer protein gene (Ltp1,) was used to indicate activity of similar genes in wheat aleurones during seed development. Northern blot analyses using a DIG-labelled barley cDNA probe showed that Ltp transcripts were present in aleurone tissue 20 dpa (FIGS. 1(a) and 1(c)). No activity was detected in early wheat grain development, 10 dpa (FIG. 1(b) but could be detected in *T turgidum* (FIG. 1(d)).

Figure 2A:
FIG. 2(a) and FIG. 2(b) show 73h germinating wheat grain.
Figure 2B:
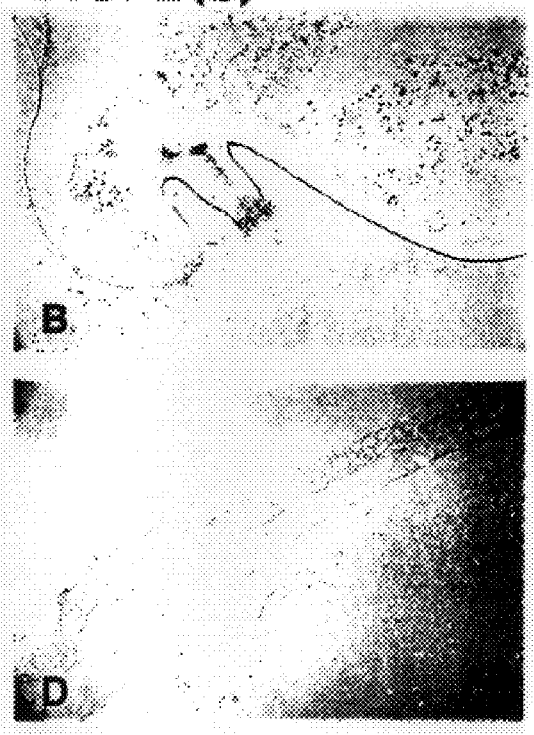
Figure 2C:
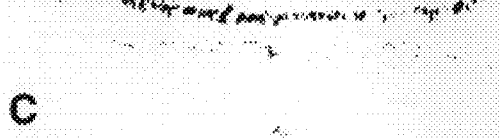
FIG. 2(c) and FIG. 2(d) show 18 dpa developing wheat grain.
Figure 2D:

In situ hybridization (based on a modification of the procedure outlined in Cox and Goldberg, 1998, Analysis of Plant Gene Expression, In Plant Molecular Biology. A Practical Approach, pp. 1–34) performed on cross sections of developing and germinating grain showed that Ltp expression was limited to aleurone cells. A $^{35}$S Ltp antisense ribo-probe hybridized strongly to aleurone cells (FIG. 2(a)), whereas no differential hybridization was observed with the sense RNA probe (FIG. 2(b)). Ltp expression was observed throughout grain development after 18 dpa and during germination up to 73 h post-imbibition at which time the endosperm was depleted. No hybridization was observed in developing endosperm, embryo or pericarp tissues (data not shown).

EXAMPLE 2

Genomic DNA of LtpW1

Genomic DNA was isolated from young leaf tissue of hexaploid wheat, (*T. aestivum*) and digested with XbaI. When this DNA was analysed by Southern blot using standard procedures and a DIG-labelled barley Ltp cDNA probe, three loci for the Ltp1 gene (at 1.5, 6.0, and 7.0 kb) were detected. The copy corresponding to the 1.5 kb XbaI band was cloned by screening a λ long C phage library of size-restricted XbaI fragments with a barley Ltp1 cDNA probe.

LtpW1 refers to the Ltp gene contained within the 1.5 kb XbaI digested *T. aestivum* genomic clone, the sequence of which is shown in SEQ ID NO: 4 (also see FIG. 3).

The coding sequence of LtpW1 shares 85% DNA identity with the barley Ltp1 (FIG. 4(a)), includes a 26 amino acid transit peptide for cell wall localization of the protein, and has one predicted 88 bp intron which is 44 bp shorter than the equivalent barley intron. The nucleoeide sequences LtpW1 and barley Ltp1 promoter (Linnestad 1991) are well conserved for approximately 140 bp upstream of the ATG start codon whereupon they diverge considerably (FIG. 4(a)). The conserved promoter region includes the putative cap and TATA sites but not the proposed CAT site or other regulatory elements (see FIGS. 3, and 4(a)).

The nucleotide sequence of the LtpW1 regulatory region exhibits little or no identity with the barley Ltp2 promoter (FIG. 4(b)). The LtpW1 regulatory region was shown to be active in aleurone of developing and germinating cereal grain which is uniquely different from the barley Ltp2 promoter which is only active during grain development but not during germination (Kalla et al 1994).

EXAMPLE 3

Expression of GUS Under the Control of LtpW1 Aleurone Regulatory Regions.

p687LtpW1-GUS

Figure 6A:
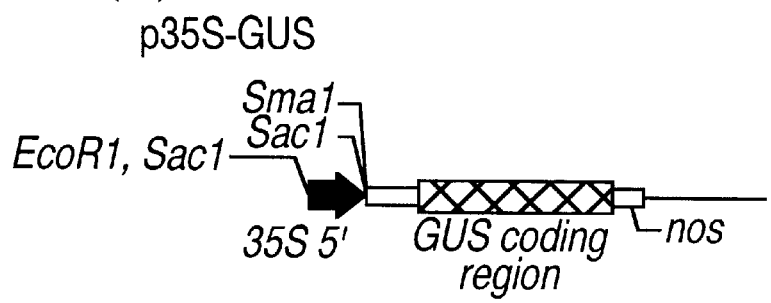
FIG. 6(a) P35s-GUS, FIG. 6(b) pACT-GUS.

A 687 bp XbaI/BcII regulatory region fragment (SEQ ID NO: 1; FIG. 3) was subcloned from pLtpW1 and fused to a GUS promoterless reporter cassette (pLC-GUS). pLC-GUS was obtained by removing the 35S promoter as a SacI fragment from pZO1016 (designated p35S-GUS herein), which was a gift from R. Sinibaldi, Sandoz, Calif. A 687 bp XbaI/BcII fragment was isolated from pTALP1 (containing the 1.5 k-b XbaI-digested *T. aestivum* genomic clone) and the sticky ends were filled-in with Klenow fragment of DNA polymerase. This fragment was blunt-end ligated into the SmaI site of pLCGUS (see FIG. 5(d)), and the orientation of the insert was checked by digesting with BamH1. The activity of this regulatory region was compared with that of the promoterless construct (pLC-GUS) as well as to constructs comprising constructive CaMV35S and rice action promoters (see FIGS. 6(a) and (b), respectively). These constructs were used for comparison of promoter activities. The 35S promoter is described in: Odel, J. T., Nagy, F. and Chua N-H (1985) Nature 313:810–812. The rice actin promoter is described in: McElroy D., Zhang, W. Cao, J. and Wu, R. (1990) Plant Cell 2:163–171.

These constructs were introduced into the aleurone of cereal grains by microparticle bombardment using standard methods. LUC and GUS constructs ware co-bombarded in equimolar amounts and GUS is expressed relative to LUC to minimize variability between reps (shots). LUC activity serves as an internal control for the shot to shot variability.

Tissues, 48 h post-bombardment, were incubated in reaction buffer containing 50 mM $NaH_2PO_4$ (pH 7.0), 10 mM EDTA and 1 mM 5-bromo-4-chloro-3-indolyl-B-glucoronide (X-Gluc), 0.5 $mMK_3[Fe(CN)_6]$, 0.5 $mMk_4[Fe(CN_6]$ at 37° C. for 4–20 h. A blue precipitate in the bombarded cells indicates activity of B-glucuronidase. The regulatory region gave high expression of GUS in histological transient assays with wheat aleurones (FIG. 7(a)). Activity was also demonstrated in maize and barley aleurones (FIG. 7(b) and (c)) The 687 bp regulatory region fragment showed no activity in leaf, root or coleoptile tissues of wheat (data not shown).

In quantitative expression assays in wheat aleurone the 687 bp regulatory region had 3.4% of the activity of the constitutive 35S promoter (Table 1). This underestimates the relative aleurone-directed ac-ivity of the LtpW1 regulatory region because of additional endosperm-derived activity of the constructive 35S promoter.

TABLE 1

Activity of p687LtpW1 in 12 dpa wheat aleurone

| Construct | Luciferase (mv/sec/ mg/ protein) | GUS (pmol MU/ min/mg protein) | GUS/LUC | %35 S Activity |
|---|---|---|---|---|
| Au | 2001 | 0 | 0 | — |
| pLC-GUS[2]/p35S-LUC | 2100 | 0 | 0 | — |
| p35S-GUS/p35S-LUC | 3400 | 30072 | 8.84 | — |
| p687LtpW1-GUS/ p35S-LUC | 4200 | 1247 | 0.3 | 3.4 |

[1]:mean of three sets of bombardments
[2]:promoterless constuct

P473LtpW1-GUS

A truncated version of the LtpW1 regulatory region (see SEQ ID NO:2; nucleotides −473 to −1 of FIG. 3; or nucleotides 214–687 of SEQ ID NO:1) was prepared by digesting pTALTP1 with HincII and BclI, and the resulting 0.47 kb fragment (after treatment with Klenow) was ligated into the Sma1 site of pLC-GUS. Orientation of the insert was checked by digesting the resulting recombinant plasmid with BamH1. The construct (p473LtpW1-GUS comprising bps 214–687 of SEQ ID NO:1, or −473 to −1 of FIG. 3) thus obtained showed 8.8% and 12.2% activity of the constitutive 35S and rice action promoters, respectively (pAct-GUS was a gift from Ray Wu at Cornell). See Table 2 for results.

TABLE 2

Activity of p473LtpW1 in 12 dpa wheat aleurone

| Construct | Luciferase (mv/sec/ mg/ protein) | GUS (pmol MU/ min/mg protein) | GUS/LUC | %35S Action Activity |
|---|---|---|---|---|
| Au | 2001 | 0 | 0 | — |
| pLC-GUS[2]/p35S-LUC | 1300 | 0 | 0 | — |
| p35S-GUS/p35S-LUC | 3500 | 8077 | 231 | — |
| pAct-GUS/p35S-LUC | 3300 | 5524 | 1.67 | — |
| p473LtpW1-GUS/ p35S-LUC | 3200 | 651 | 0.2 | 88 12.2 |

[1]:mean of three sets of bombardments
[2]:promoterless construct

When compared within a single experiment, the 473 bp fragment (bps 214–687 of SEQ ID NO:1, or −473 to −1 of FIG. 3) was 170% as active as the 687 bp fragment (Table 3).

TABLE 3

Activity of p687LtpW1, p473LtpW1, and P206LtpW1 in 7 dpa wheat aleurone

| Construct | Luciferase (mv/sec/ mg/ protein) | GUS (pmol MU/ min/mg protein) | GUS/LUC | %35 S Activity |
|---|---|---|---|---|
| pLC-GUS[2]/p35S-LUC | 97001 | 120 | 0.01 | 0.1 |
| p35S-GUS/p35S-LUC | 2300 | 18305 | 7.96 | — |
| p206LtpW1-GUS/ p345S-LUC | 7900 | 1781 | 0.23 | 2.9 |
| p473LtpW1-GUS/ p35S-LUC | 6800 | 2399 | 0.35 | 4.4 |
| p687LtpW1-GUS/ p35S-LUC | 5100 | 1090 | 0.21 | 2.6 |

[1]:mean of three sets of bombardments
[2]:promoterless construct

P206LtpW1-GUS

To generate p206LtpW1 GUS, pTALTP1 was digested with BclI, then with HindIII, and the 0.2 kb fragment was isolated from a gel and purified. The sticky ends were filled in with Klenow and the resulting fragment was ligated into the Sma1 site of pLC-GUS. Neither e 687 bp or 473 bp regulatory regions was active in leaf tissue but the 206 bp HinII/BclI tncated regulatory region (SEQ ID NO:3; nucleotides −206 to −1 of FIG. 3; nucleotides 481–687 of SEQ ID NO:1) had 7.5% the activity of the 35S promoter in leaf (Table 4).

TABLE 4

Activity of p687LtpW1, p473LtpW1, and p206LtpW1 in wheat leaf tissue

| Construct | Luciferase (mv/sec/ mg/ protein) | GUS (pmol MU/ min/mg protein) | GUS/LUC | %35 S Activity |
|---|---|---|---|---|
| pLC-GUS[2]/p35S-LUC | 2001 | 1.6 | 0.007 | 0.7 |
| p35S-GUS/p35S-LUC | 200 | 204.3 | 1.02 | — |
| p206LtpW1-GUS/ p35S-LUC | 200 | 15.3 | 0.077 | 7.5 |
| p473LtpW1-GUS/ p35S-LUC | 700 | 1.3 | 0.002 | 0.2 |
| p687LtpW1-GUS/ p35S-LUC | 700 | 1.7 | 0.002 | 0.2 |

[1]:mean of three sets of bombardments
[2]:promoterless construct

Similarly, in wheat scutellum tissue, only the 206 bp regulatory region fragment was active (Table 5) with activities of 11.4% of 35S and 8.5% of rice actin promoters.

TABLE 5

Activity of p687LtpW1, p473LtpW1, aud p206LtpW1 in 20 dpa wheat scutellum tissue

| Construct | Luciferase (mv/sec/ mg/ protein) | GUS (pmol MU/ min/mg protein) | GUS/LUC | %35 S Activity |
|---|---|---|---|---|
| pLC-GUS[3]/p35S-LUC | 13001 | 37 | 0.028 | 0.23, 0.17 |
| p35S-GUS/p35S-LUC | 400 | 4873 | 12.182 | — |
| pAct-GUS/p35S-LUC | 400 | 6530 | 16.325 | — |
| p206LtpW1-GUS/ p35S-LUC | 100 | 139 | 1.39 | 11.41, 8.51 |
| p473LtpW1-GUS/ | 200 | 2 | 0.01 | 0.08, |

TABLE 5-continued

Activity of p687LtpW1, p473LtpW1, aud p206LtpW1 in 20 dpa wheat scutellum tissue

| Construct | Luciferase (mv/sec/ mg/ protein) | GUS (pmol MU/ min/mg protein) | GUS/LUC | %35 S Activity |
|---|---|---|---|---|
| p35S/LUC | | | | 0.06 |
| p687LtpW1-GUS/ | 200 | 6 | 0.03 | 0.24, |
| p35S-LUC | | | | 0.18 |

[1]:mean of three sets of bombardments
[2]:promoterless construct

Thus the nucleotide sequence between 206 bp and 473 bp (i.e. −206 to −473 of FIG. 3, or 481–214 of SEQ ID NO:1) determines the tissue and stage dependent regulation of the LtpW1 regulatory region.

Collectively, these data indicate that:

nucleotides 1–214 of SEQ ID NO:1 (i.e., the portion of the promoter that is included in p687LtpW1 and not included in p473LtpW1, bps −687 to −473 of FIG. 3) and 215–481 of SEQ ID NO:1 (bps −472 to −206 of FIG. 3) are responsible for imparting tissue specificity within this regulatory region. Removal of either of these regions from the full length regulatory region results in greatly reduced tissue specificity (Table 4).

the region comprising nucleotides 1–481 of SEQ ID NO: 1 (bps −687 to −206 of FIG. 3) is responsible for regulating the strength of regulatory region activity, and includes both silencer- and enhancer-type activities:

the fragment comprising nucleotides 214–481 of SEQ ID NO:1 (bps −473 to −206 of FIG. 3) exhibits enhancer-like activity as constructs comprising this region (e.g. p473LtpW1) resulted in increased expression when compared with either the full length regulatory region (p687LtpW1), or the truncated regulatory region p206LtpW1 (see Table 3). Similarly, nucleotides 482–687 of SEQ ID NO:1 (bps −205 to −1 of FIG. 3) also exhibit enhancer-type activity, since constructs comprising this region (p206LtpW1) exhibited higher levels of expression than the full length regulatory region;

the fragment comprising nucleotides 1–214 of SEQ ID NO:1 (bps −687 to −473 of FIG. 3) comprises silencer-type elements as constructs comprising this region (e.g. p687LtpW1) result in lower levels of expression compared with the levels of expression obtained with either of the truncated regulatory region constructs, p206LtpW1, or p473LtpW1 (see Table 3);

the 206 bp version of the LtpW1 regulatory region (i.e., 481–687 of SEQ ID NO:1, or bps −206 to −1 of FIG. 3) represents a novel, constitutive promoter, for monocotyledonous plants.

Because of the relatively superior activity of the 473 bp fragment (i.e. 214–687 of SEQ ID NO:1, or bps −473 to −1 of FIG. 3) in aleurone tissue (Tables 1, 2 and 3), this version was used for transformation of maize.

EXAMPLE 4
Preparation of Transgenic Plants of Zea mays

Figure 6B:
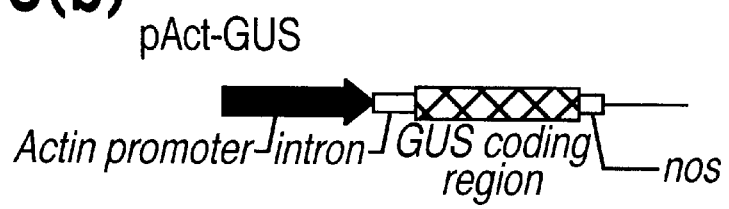
FIG. 6 shows two constructs used for comparative studies containing prior art promoters.

To verify that the 5' flanking sequence from the genomic clone LtpW1 contained the regulatory sequences required to confer expression in aleurone cells, the 473 bp LtpW1/GUS fusion was co-bombarded with a bialaphos selectable plasmid (pAHC25) into embryogenic cultures of raize. Transgenic calli were selected on bialaphos media and transgenic plants regenerated. The transgenic plants were screened for GUS activity. The 473 bp LtpW1 regulatory region directed The expression of GUS only in the aleurone layer of developing and germinating transgenic maize kernels (FIG. 6).

EXAMPLE 5
Stable Expression of a Gene of Interest in Monocots Under the Control of p206LptW1.

Figure 10:
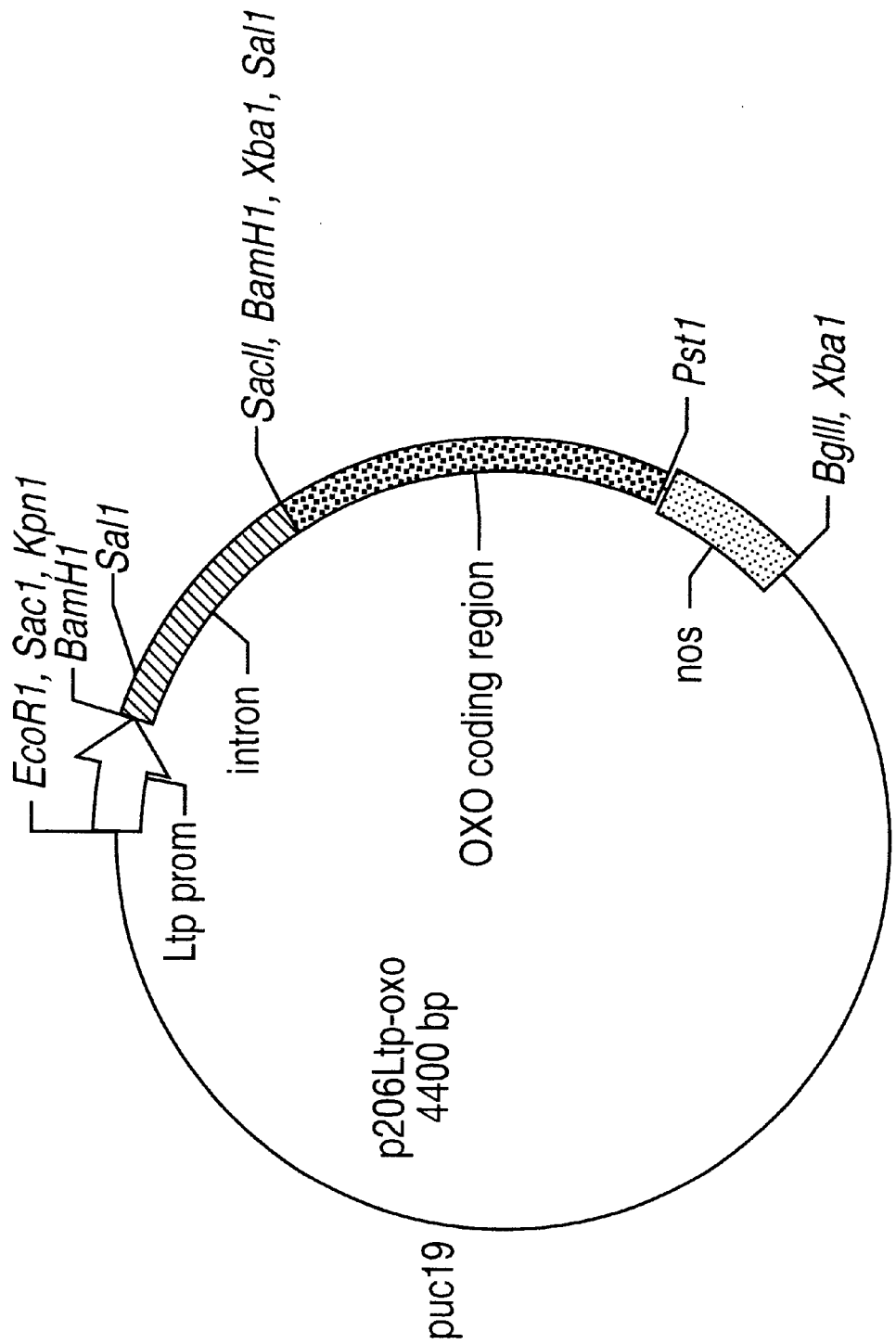
FIG. 10 shows a diagrammatic representation of the p206Ltp-oxo plasmid comprising the 206 fragment of the Ltp regulatory region (Lpt prom), adjoining an intron and the oxo coding region.
Figure 11:
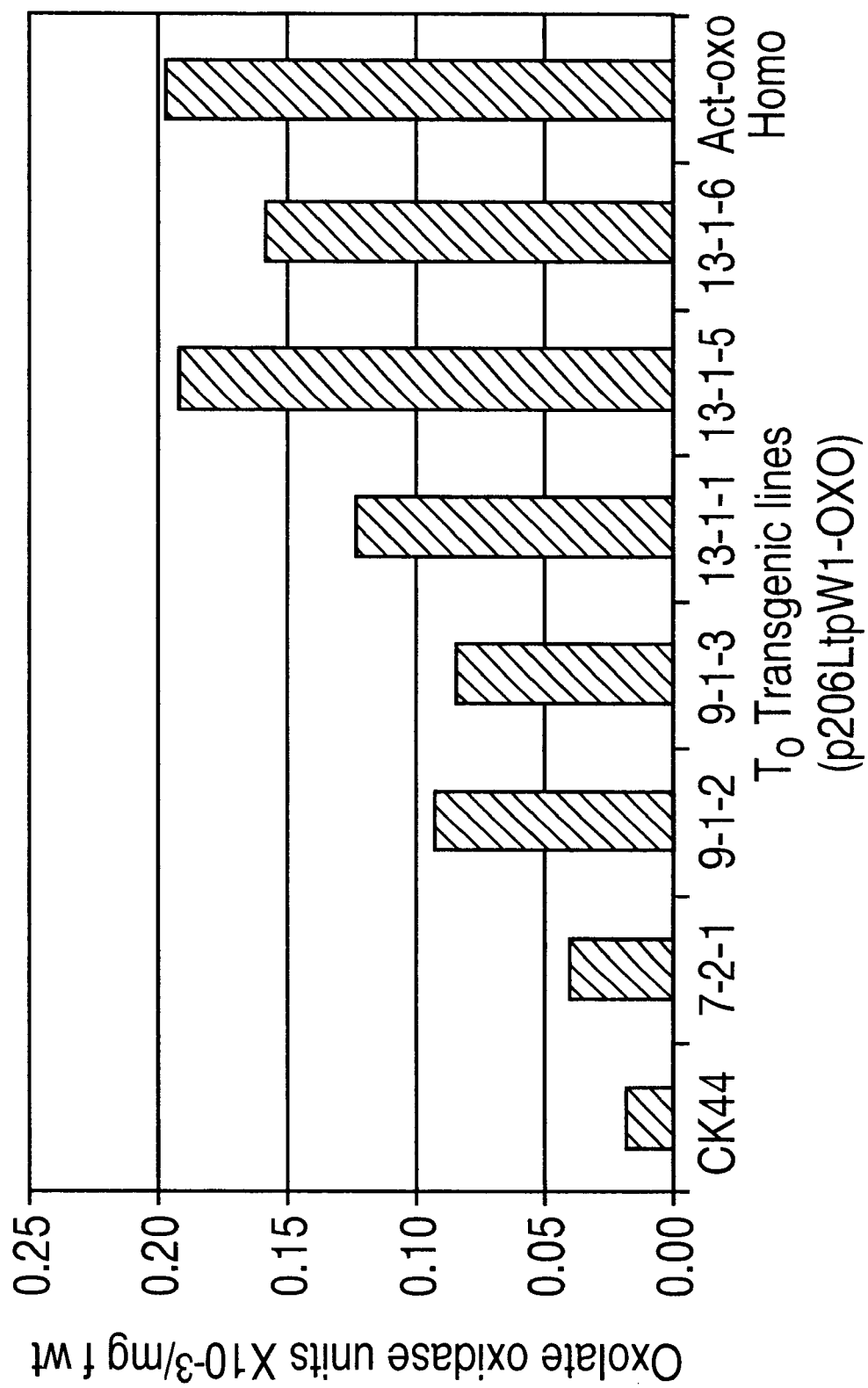
FIG. 11 shows the expression of p206Ltp-oxo in leaf tissue of transgenic corn.

Several lines of corn were stably transformed via particle bombardment as described above (Example 4) with a p206Ltp-OXO construct (FIG. 10) which generates oxalate oxidase reporter activity (Byron Lane et al., J. Biol. Chem. 1991, 266:10461–10469). This construct also contains an intron, for example the IVS6 intron, or the first intron from the actin gene. Plants were also transformed with oxalate oxidase under the control of the strong monocot rice actin promoter (McElroy D., Zhang, W., Cao, J., and Wu, R. 1990. Plant Cell 2:163–171). Plant tissues were harvested and assayed for oxalate oxidase activity. Plants comprising the oxalate oxidase transgene under the control of p206LtpW1 exhibited substantially higher activity than the non-transformed CK44 line. Line 13-1-5 expressed at 95% of the level observed in a line homozygous for the oxalate oxidase transgene. under the control of the rice actin promoter (FIG. 10).

EXAMPLE 6
Activity of p2D6Lpt in Dicotyledons

The activity of the 206 bp HinII/BcII truncated regulatory element (SEQ ID NO3; FIG. 3) was also examined within dicotyledonous plants to determine whether this regulatory element is active within these plants. Constructs comprising GUS in operative association with p206LptW1 were prepared as outlined in Example 3, however, an intron (either the IVS6 or actin intron) was included. These constructs were introduced into several dicotyledonous plants via particle bombardment as outlined in Example 3. A chimeric construct comprising p206LptW1, linked with the BstY1 fragment of T1275, an enhancer element obtained from tobacco (see U.S. Pat. No. 5,824,872, which is incorporated herein by reference), and in operative association with GUS, was also examined. The activities of the constructs comprising the p206Lpt regulatory region was compared with the activity of the strong monocot rice actin promoter (McElroy D., Zharg, W., Cao, J., and Wu, R. 1990. Plant Cell 2:163–171). The results are present in Table 6.

TABLE 6

Activity of p-206LtpW1-GUS in leaf tissue of dicotyledonous plants and regulation by an enhancer element, BstY1

| Plasmid | Gus Positive Foci per Shot | | |
|---|---|---|---|
| | Soya | Brassica | Nicotiana |
| Au* | 0[1] | 0 | 0 |
| pAct-GUS | 0 | 0 | 6 |
| p206LtpW1-GUS | 3 | 123 | 48 |
| pBstY1-206LtpW1-GUS** | 133 | 91 | 155 |

[1]Mean of three bombardments, assayed 48 hours post-bombardment.
*AU is a gold control, no added DNA.
**BstY1 is the −394 to −62 fragment of T1275 regulatory region (U.S. Pat. No. 5,824,872).

The rice actin monocot expression vector (pAct-GUS) had no activity in Soya and Brassica and low activity in Nicoriana leaves. However, the 206LtpW1 regulatory region was active in Soya, Brassica and Nicoriana and exhibited substantially greater activity than the actin promoter in Brassica and Nicoriana.

These results indicate that the truncated LtpW1 regulatory region, 206LtpW1 (SEQ ID NO 3) is subject to regulation by chimeric enhancer fragments such as the BstY1 element of T1275 (U.S. Pat. No. 5,824,872). The 206LtpW1 regulatory region with the BstY1 enhancer element had uniformly high activity in the dicotyledonous plants investigated.

Collectively these results indicate that the truncated regulatory region, p206Ltp, is active in a range of monocot and dicot plants, and its regulatory activity may be modulated in the presence of other exrogenous regulatory elements.

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A chimneric regulatory element comprising:
   i) a first regulatory element comprising the nucleotide sequence of SEQ ID NO:3, or a nucleoride sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., and exhibits regulatory element activity; and
   ii) a second regulatory element, said second regulatory element comprising at least one exogenous mediator of the regulatory activity of said first regulatory element.

2. The chimeric regulatory element of claim 1, wherein said first regulatory element exhibits constitutive activity.

3. The chimeric regulatory element of claim 2, wherein said second regulatory element is an enhancer element or a silencer element.

4. The chimeric regulatory element of claim 3, wherein said second regulatory element is an enhancer element.

5. The chimeric regulatory element of claim 4, wherein said enhancer element is selected from the group consisting of a 35S enhancer, an actin enhancer, and a BstY1 fragment of T1275.

6. A vector comprising the chimeric regulatory element of claim 1 in operative association with a gene of interest.

7. An expression vector comprising the chimeric regulatory element of claim 1 in operative association with a gene of interest.

8. A transformed plant cell culture comprising the vector of claim 6.

9. A transgenic plant transformed with the vector of claim 6.

10. The transgenic plant of claim 9, wherein the plant is a monocotyledonous plant.

11. The transgenic plant of claim 9, wherein the plant is a dicotyledonous plant.

12. A transformed plant cell culture comprising the expression vector of claim 7.

13. A transgenic plant transformed with the expression vector of claim 7.

14. The transgenic plant of claim 13, wherein the plant is a monocotyledonous plant.

15. The transgenic plant of claim 13 wherein the plant is a dicotyledonous plant.

16. A transgenic dicotyledonous plant comprising a gene construct, said gene construct comprising:
   i) the nucleotide sequence of SEQ ID NO:3 or a nucleotide sequence that hybridizes to the nucleotide sequence of SEQ ID NO:3 under the following conditions: hybridization in 5×SSC and 50% formamide at 42° C.; and washing in from about 0.5×SSC to about 0.2×SSC at 65° C., wherein said nucleotide sequence exhibits regulatory element activity; and
   ii) a gene of interest in operative association with said nucleotide sequence.

17. A method of expressing a gene of interest within a plant comprising:
   i) a gene of interest for which expression is desired in operative association with the chimeric regulatory region of claim 1 to produce a gene of construct; and ii) introducing said gene construct into said plant and allowing for expression of said gene of interest.

18. The method of claim 17 wherein said plant is a monocotyledonous plant.

19. The method of claim 17 wherein said plant is a dicotyledonous plant.

20. A method of expressing a gene of interest within a dicotyledonous plant comprising:
  i) a gene of interest for which expression is desired in operative association with the nucleotide sequence of SEQ ID NO:3 or a nucleotide sequence that hybridizes to the nucleotide sequence of SEQ ID NO:3 under the following conditions:
  hybridization in 5×SSC and 50% formamide at 42° C.; and washing in from about 0.5×SSC to about 0.2× SSC at 65° C., wherein said nucleotide sequence exhibits regulatory element activity, to produce a gene construct; and
  ii) introducing said gene construct into said dicotyledonous plant and allowing for expression of said gene of interest.

* * * * *